United States Patent [19]
Vincent et al.

[11] Patent Number: 5,872,102
[45] Date of Patent: Feb. 16, 1999

[54] METHOD FOR ISOLATION OF BOVINE LOW-MOLECULAR WEIGHT CR-BINDING SUBSTANCE AND METHOD OF USE OF THE SAME

[75] Inventors: John B. Vincent; C. Michele Davis, both of Tuscaloosa, Ala.

[73] Assignee: The University of Alabama, Tuscaloosa, Ala.

[21] Appl. No.: 729,591

[22] Filed: Oct. 11, 1996

[51] Int. Cl.$^6$ ..................................................... C07K 19/00
[52] U.S. Cl. ............................................. 514/21; 530/350
[58] Field of Search ................................ 530/350; 514/21

[56] References Cited

PUBLICATIONS

Akiko Yamamoto et al., "Distribution and Chromium–Binding Capacity of A Low–Molecular–Weight, Chromium–Binding Substance In Mice", *Journal Of Inorganic Biochemistry*, vol. 22, pp. 91–102, 1984.

John B. Vincent, "Relationship Between Glucose Tolerance Factor And Low–Molecular–Weight Chromium–Binding Substance", *Journal of Nutrition*, vol. 124, pp. 117–118, 1994.

Akiko Yamamoto et al., "isolation Of A Biologically Active Low–Molecular–Mass Chromium Compound From Rabbit Liver", *European Journal Of Biochemistry*, vol. 165, pp. 627–631, 1987.

John B. Vincent, "Chromium: Biological Relevance", *Encyclopedia Of Inorganic Chemistry*, vol. 2, pp. 661–665, 1994.

Akiko Yamamoto et al., "Purification And Properties Of Biologically Active Chromium Complex From Bovine Colostrum", *Journal of Nutrition*, vol. 118, pp. 39–45, 1987.

Yamamoto, Caplus An #1989:550993 1989.

Yamamoto, Caplus An#1981:526830 1981.

*Primary Examiner*—Cecilia J. Tsang
*Attorney, Agent, or Firm*—Oblon, Spivak, McClelland, Maier & Neustadt. P.C.

[57] ABSTRACT

A fully chromium loaded bovine low-molecular weight chromium-binding protein is isolated by a process that combines homogenization with supplementation of chromium content. Following homogenization with water, the homogenate is fractionated with ethanol, and the fractions obtained are subjected to serial chromatography (ion-exchange followed by size-exclusion chromatography) to obtain the biologically pure bovine LMWCr. This biologically pure material elutes from an HPLC column as essentially a single band, giving a high degree of purity. The LMWCr is useful as a dietary supplement, and for the treatment or prevention of a variety of chromium-related disease conditions.

7 Claims, 7 Drawing Sheets

METHOD FOR ISOLATION OF BOVINE LOW-MOLECULAR WEIGHT CR-BINDING SUBSTANCE AND METHOD OF USE OF THE SAME

BACKGROUND OF THE INVENTION

Field of the Invention

This invention deals with a purified, biologically active source of chromium, and methods of administration thereof. Specifically, purified bovine low-molecular weight chromium-binding protein (LMWCr) is isolated from bovine liver, and methods of administration are provided.

BACKGROUND OF THE PRIOR ART

Chromium has long been recognized as an essential trace element in mammals, and determined to be required for normal carbohydrate and lipid metabolism. See, e.g., Vincent, *Encyclopedia of Inorganic Chemistry,* 2,661–665 (1994). Cr deficiency in humans results in symptoms comparable to those associated with adult-onset diabetes and cardiovascular disease. See, e.g., Anderson, *Clin. Physiol. Biochem.,* 4, 31–41 (1986), Mertz, *J. Nutr.,* 123, 626–33 (1993) and Riales et al, *Am. J. Clin. Nutr.,* 34, 2670–2678 (1981).

Two materials are currently commercially available as chromium dietary supplements intended as diet or exercise training aids to increase muscle and reduce fat: chromium picolinate and glucose tolerance factor from Brewer's yeast. Both appear to be good sources for chromium that can be absorbed by the body when compared to the absorption of simple inorganic chromium salts. However, some research laboratories have been unable to reproduce experimental results on glucose tolerance factors; at certain concentrations it can also inhibit insulin, which negates its beneficial effects. Instead of glucose tolerance factor Brewer's yeast, or Brewer's yeast enriched with chromium are also commercially available. The yeast, however, has an unpleasant aroma and taste, which is extremely difficult to mask. On the other hand, chromium picolinate has been shown to cause chromosomal damage. Sterns et al, *FASEB,* 9, A451 (1995). Additionally, these materials appear to serve only as readily absorbable sources of Cr. McCarty, *J. Optimal Nutr.,* 2, 36–53 (1993). Kinetic studies demonstrate no biological activity for the compounds themselves.

Various symptoms associated with Cr deficiencies include increased concentration of circulating insulin, decreased insulin receptor number, elevated cholesterol and triglyceride levels and reduced high-density lipoprotein cholesterol levels. See, e.g., Mertz et al, *Am. J. Physiol.,* 209, 489–494 (1965), Anderson, *Trace Elements in Human and Animal Nutrition,* Vol. 1, 225–244 (1987) and Riales et al, *Am. J. Clin. Nutr.,* 34, 2670–2678 (1981). While glucose tolerance improvement has been demonstrated repeatedly after supplementation of the diet with chromium, see, e.g., Mahdi et al, *Ann. Nutr. Metab.,* 35, 65–70 (1991), as much as ninety percent of the American population and half of the population of developed nations' daily intake less than the recommended safe and adequate quantities of Cr. Anderson, *Risk Assessment of Essential Elements,* 187–196 (1994).

Unlike artificial chromium sources or non-mammalian Cr sources, a biologically active Cr-containing material from proteins could prove to be an optimal nutritional supplement, as it has intrinsic biological activity. This species was identified by a group of nutritionists in Japan and named low-molecular weight chromium-binding substance (LMWCr). Yamamoto et al in the following references: *European Journal of Biochemistry,* 165, 627–631 (1987); *Toxicology and Applied Pharmacology,* 59, 515–523 (1981); *Environmental Research,* 32, 228–239 (1983); *Journal of Inorganic Biochemistry,* 22, 91–102 (1984), *Journal of Nutrition,* 118, 39–45 (1987) and *Biochemical and Biophysical Research Communications,* 163, 189–193 (1989).

Unfortunately, LMWCr in vivo does not contain a full complement of chromium. Chromium-loading was accomplished by these workers by injecting mice, dogs or rabbits with chromate solutions, waiting a period of time, and then removing the liver of the mammals. Using this procedure, only micrograms of purified LMWCr could be purified and isolated. Micrograms of LMWCr have also been isolated from bovine colostrum without using a chromium-loading procedure. These procedures are inadequate for the isolation of appreciable quantities of LMWCr. The procedure also makes the other tissue from these animals inedible, as a result of the chromate addition (chromate is extremely toxic). Therefore, using larger mammals such as pigs or cows in this process would be impractical.

Accordingly, it remains an object of those of skill in the art to develop a method for providing LMWCr as a chromium source for mammals, in substantially pure form, in bulk quantity.

SUMMARY OF THE INVENTION

The above objects, and others made more clear by the discussion following, are met by a process for isolation of bovine LMWCr in substantial amounts. To improve chromium loading, bovine liver is homogenized with one volume of water containing either a chromium (VI) or chromium (III) source followed by fractionation by ethanol precipitations, ion-exchange chromatography and size exclusion chromatography. After the ethanol precipitations, all chromium present exists as chromium (III). Optimal results have been obtained, by employing, in the homogenization step, 3.4 mmoles of chromium, as dichromate, per two liters of homogenate. One liver (approximately 10–12 kg of tissue) yields approximately 30 mg of purified LMWCr. The isolated material elutes as a single band upon Shodex (size exclusion) HPLC chromatography, giving a high degree of purity. LMWCr is not an artifact from proteolytic degradation as inclusion of protease inhibitors in the water used in homogenization has no effect on the yield or properties of the material.

The isolated bovine liver LMWCr can be used as a dietary supplement for humans, or as a substance for various treatments, exercise aid, etc. Given the high activity of LMWCr, as contrasted with currently available chromium complexes, a relatively low dosage value of micrograms of chromium would be required, per day.

DETAILED DESCRIPTION OF THE INVENTION

Figure 1:
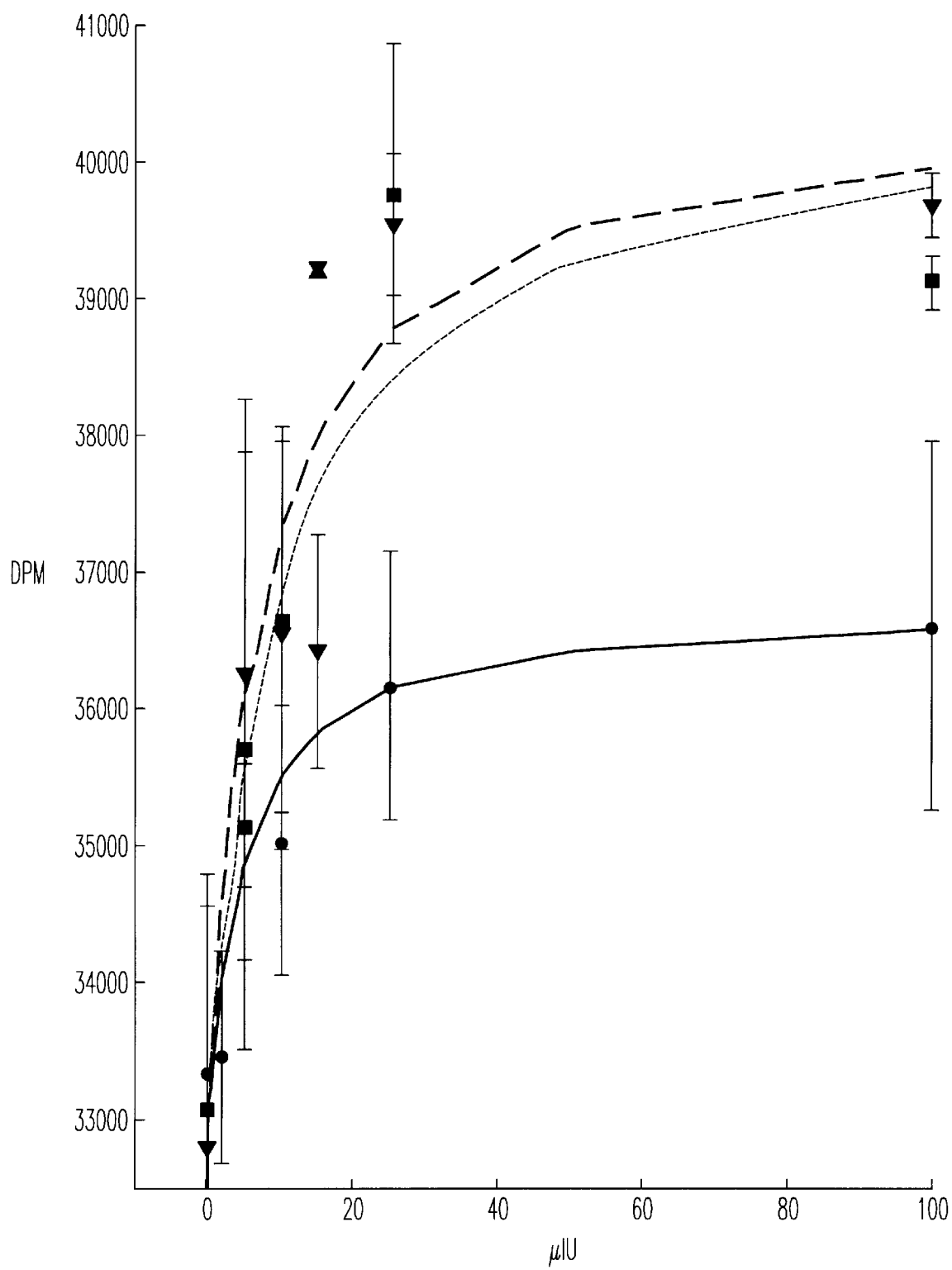
FIG. 1. Insulin dose response curve for $^{14}C$ incorporation from [U-$^{14}C$] glucose into lipid by rat adipocytes in the presence of varying concentrations of chromium as bovine liver LMWCr. The lines represent the best fit curves to the data using a hyperbolic function. Solid circles, control (no added chromium); solid triangles, 2 ng chromium; solid squares, 20 ng chromium.

This invention begins with recognition that while isolation of LMWCr from other mammalian livers has previously been achieved, no yield has been obtained from mammalian livers that would allow bulk preparation of this material as a supplement in amounts adequate for human purposes, or otherwise suitable for administration to mammals.

We have now developed a procedure for isolating LMWCr in much greater quantity than the microgram quantities previously available. Previous efforts to isolate LMWCr, utilizing sources including rabbit liver, dog liver and cow colostrum required the sacrifice of huge numbers of individuals or the use of unreasonable volumes to attempt to isolate substantial quantities. Given the high concentration of LMWCr in liver and its availability in bulk, bovine liver was chosen as a source of the polypeptide; additionally bovine liver is inexpensive (calf liver—not bovine liver—is the liver commonly consumed as food).

To guarantee the material contained its full complement of chromium, an in vitro chromium loading procedure was developed which required the addition of 3.4 mm of chromium as dichromate per 2 liters of homogenate. Previous studies with untreated mice indicated that addition of Cr to the liver cytosol in vitro results in incorporation of Cr into LMWCr to higher levels than by in vivo procedures (Yamamoto et al 1984). This is a key step. Yamamoto and coworkers either injected the animal in advance with chromate to load LMWCr with chromium or added chromate to cytosol preparations. Chromate is a very potent carcinogen. Injecting a cow with chromium would make the meat from the entire animal unsuitable for human consumption and is thus not feasible from a financial standpoint. Preparation of cytosol requires ultracentrifugation of samples at circa 100, 000×g; only very small samples (only a few milliliters) can be centrifuged at this rate at a time, making bulk preparation of LMWCr impossible. Thus, addition of chromium to the homogenization buffer is crucial. From 5 to 6 kg of diced tissue, approximately 30 mg of LMWCr can be isolated; the material elutes as a single band upon Shodex (size exclusion) HPLC chromatography and migrates as a single band in SDS PAGE, indicating a high degree of purity. This Cr-loading procedure also results in a 5-fold higher yield of LMWCr per gram tissue than the published in vivo procedure with rabbit liver. When chromate addition is not used, only trace quantities of the polypeptide can be isolated; however, the protein is still present, indicating it is naturally occurring.

Therefore, LMWCr is maintained in liver cells as the apoprotein (at least well in excess of 90%), which may have implications for its function. (Chromic salts can also be added in place of chromate salts as a source of chromium, although levels of chromium incorporation are reduced) . Likewise, our use of a protease inhibitor cocktail in the water used for extraction and homogenization and in subsequent buffers (comprised of 3 mM benzamide, 0.5 mM phenylmethylsulfonyl fluoride, and 350 nM pepstatin A) has no effect on the yield of the protein; again suggesting the protein is not an artifact, resulting from proteolytic degradation. The use of EDTA as an inhibitor was avoided as it could compete for the added chromium. The use of the protease inhibitor cocktail during initial steps of the purification is now routine as the amount of extraneous polypeptides to be separated from LMWCr is greatly reduced.

We have also examined the ability to obtain LMWCr from other mammalian sources. To compete as a source, the mammalian tissue must be available in bulk; consequently we have focused on porcine tissue (Sumrall & Vincent, unpublished results). Porcine LMWCr unfortunately is unstable, being susceptible to hydrolysis. Whereas bovine LMWCr can be stored as a buffered aqueous solution for days at 4° C., porcine LMWCr shows marked decomposition in hours and can almost completely denature and lose all biological activity at this temperature in days. The hydrolysis product is an inhibitor of biological activity, amplifying the problem. [Porcine LMWCr was obtained from porcine kidney and loaded with Cr in an identical fashion]. This makes bovine liver all the more important as a source of LMWCr.

LMWCr has many important properties for use as a nutritional supplement. It has intrinsic biological activity (FIG. 1), has a low molecular weight which should facilitate absorption, contains four chromic ions per molecule, and has a much larger $LD_{50}$ than chromate or chromium (III) salts (i.e., is much less toxic). Importantly, we have established the biological function of LMWCr. Insulin dose dependence studies of glucose incorporation into carbon dioxide and lipid by isolated rat adipocytes in the presence of varying concentrations of LMWCr have indicated that LMWCr has a role in the potentiation of insulin action subsequent to the binding of insulin to the receptor. Given the kinetic inertness of Cr(III) complexes such that LMWCr is not expected to have any type of enzymatic function, a role for LMWCr in regulation of phosphorylation/dephosphorylation events is indicated. While LMWCr appears to activate a membrane phosphotyrosine phosphatase, we have shown that LMWCr's primary function lies in the activation of insulin receptor tyrosine protein kinase activity in response to insulin.

Figure 2:
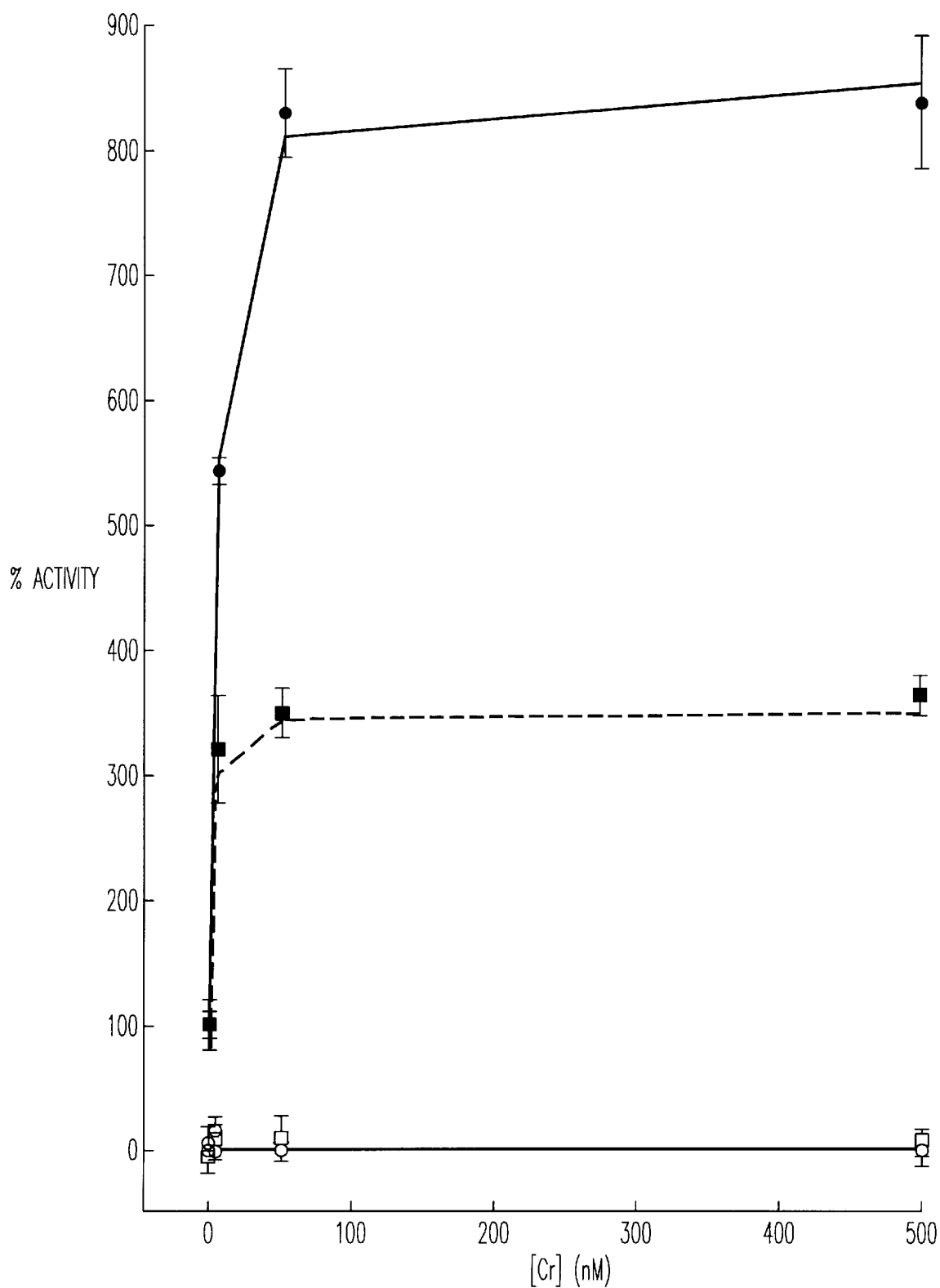
FIG. 2. Activation of rat adipocytic membrane protein tyrosine kinase activity using 0.75 $\mu M$ fragments of cell division kinase p34cdc2 (amino acids 6–20) (circles) and gastrin (amino acids 1–17) (squares) as substrates by bovine liver LMWCr in the presence (solid symbols) or absence (open symbols) of 100 nM insulin. Zero percent activity corresponds to kinase activity in the absence of insulin. Phosphotyrosine was assayed using a protein kinase assay kit (Boehringer Mannheim). 24 μL of rat adipocyte membrane suspension corresponding to 310 μg protein/mL was utilized. Bovine pancreas insulin was from Sigma. The curves represent best fit hyperbolic curves. The assay was performed in 50 mM Tris (Tris-(hydroxymethyl) aminomethane), pH 7.4 containing 0.75 mM ATP and 0.7 mM MgCl$_2$ at 37° C. for 75 minutes. All measurements were performed in triplicate; error bars represent standard deviation. LMWCr interacts with one of the assay kit components (in the absence of ATP and membranes) resulting in changes in the background absorbance of the assay; these contributions have been subtracted from all data.

The addition of bovine liver LMWCr to rat adipocytic membranes in the presence of 100 nM insulin results in a concentration dependent 3.5 to 8 fold stimulation of insulin-dependent protein tyrosine kinase activity using a fragment of gastrin and cell division p34cdc2 as substrates, respectively, while no activation of kinase activity with either substrate is observed in the absence of insulin (FIG. 2). The dependence of the activations on the concentration of LMWCr can be fit to a hyperbolic curve to give dissociation constants (Km's) of approximately 875 pM. Addition of polyclonal antibodies whose epitope corresponds to amino acids 29–48 mapping at the amino terminus of the precursor form of the human insulin receptor a chain (the region contains amino acid residues believed to be essential in the binding of insulin to the α subunit; the α subunits of insulin receptor are external to the cell membrane) to the rat adipocytic membranes in the presence of 100 nM insulin results in a loss of the activation of insulin receptor kinase activity (FIG. 2). Thus, LMWCr significantly potentiates a membrane kinase activity only in the presence of insulin, and preventing the binding of insulin to its receptor eliminates the ability of LMWCr to potentiate kinase activity. Given that the membrane preparations should be devoid of soluble, physiological insulin receptor kinase substrates, such as insulin receptor substrate 1 (IRS-1), these results suggest that the site of action of LMWCr is the insulin receptor itself.

Figure 3A:
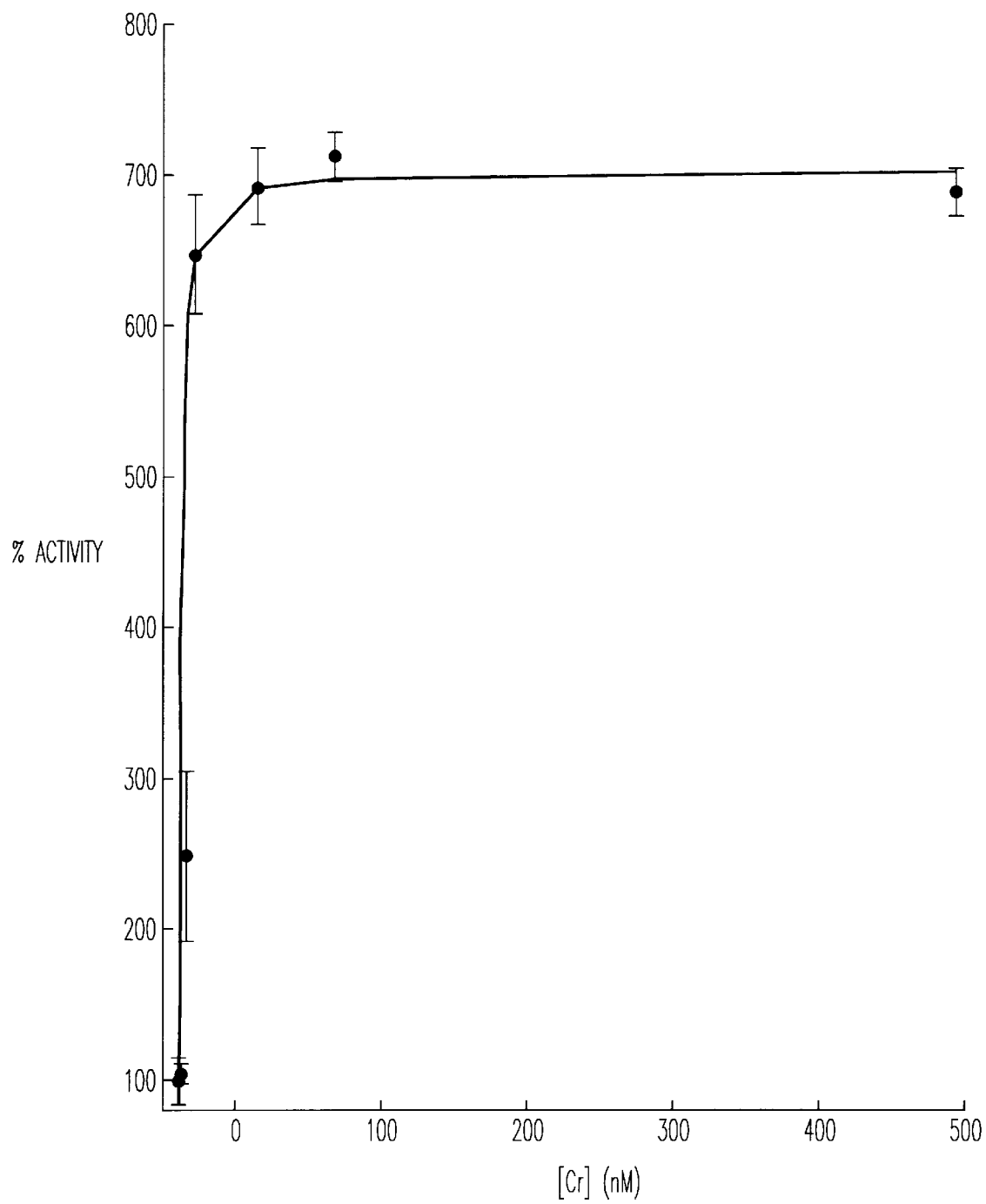
FIGS. 3A and 3B. 3A—Activation of protein tyrosine kinase activity of isolated rat liver insulin receptor by bovine liver LMWCr using a fragment of gastrin (0.75 μM) as substrate in the presence of 100 nM insulin. Rat liver insulin receptor was obtained from Sigma. The receptor was incubated with insulin for 2 hours at circa 4° C. prior to the assay in 67 mM Hepes (N-2hydroxyethylpiperazine-N'-2-ethanesulfonic acid) buffer, pH 7.4 containing 0.06 percent Triton-X 100, 0.3M NaCl, 12 mM MgCl$_2$, 2 mM MnCl$_2$, 0.1M sodium acetate, and 100 mg/mL bovine serum albumin. The hydrolysis reaction was performed for 75 minutes at 37° C. after being initiated by addition of ATP to give a final ATP concentration of 0.75 μM. (B) activation of protein tyrosine kinase activity of rat adipocytic membranes in the presence (squares) and absence (circles) of polyclonal antibodies whose epitope corresponds to amino acids 29–48 mapping at the amino terminus of the precursor form of human insulin receptor α chain using a fragment of gastrin as substrate in the presence of 100 nM insulin by LMWCr. Polyclonal antibodies were obtained from Santa Cruz Biotechnology. 25 μL of a rat adipocytic membrane suspension corresponding to 40 μg protein/mL was utilized. 0.7 μg antibodies were incubated with the membranes for 2 hours at circa 4° C. prior to the initiation of the reaction by addition of ATP. Other parameters are as described in the caption to FIG. 1.
Figure 3B:
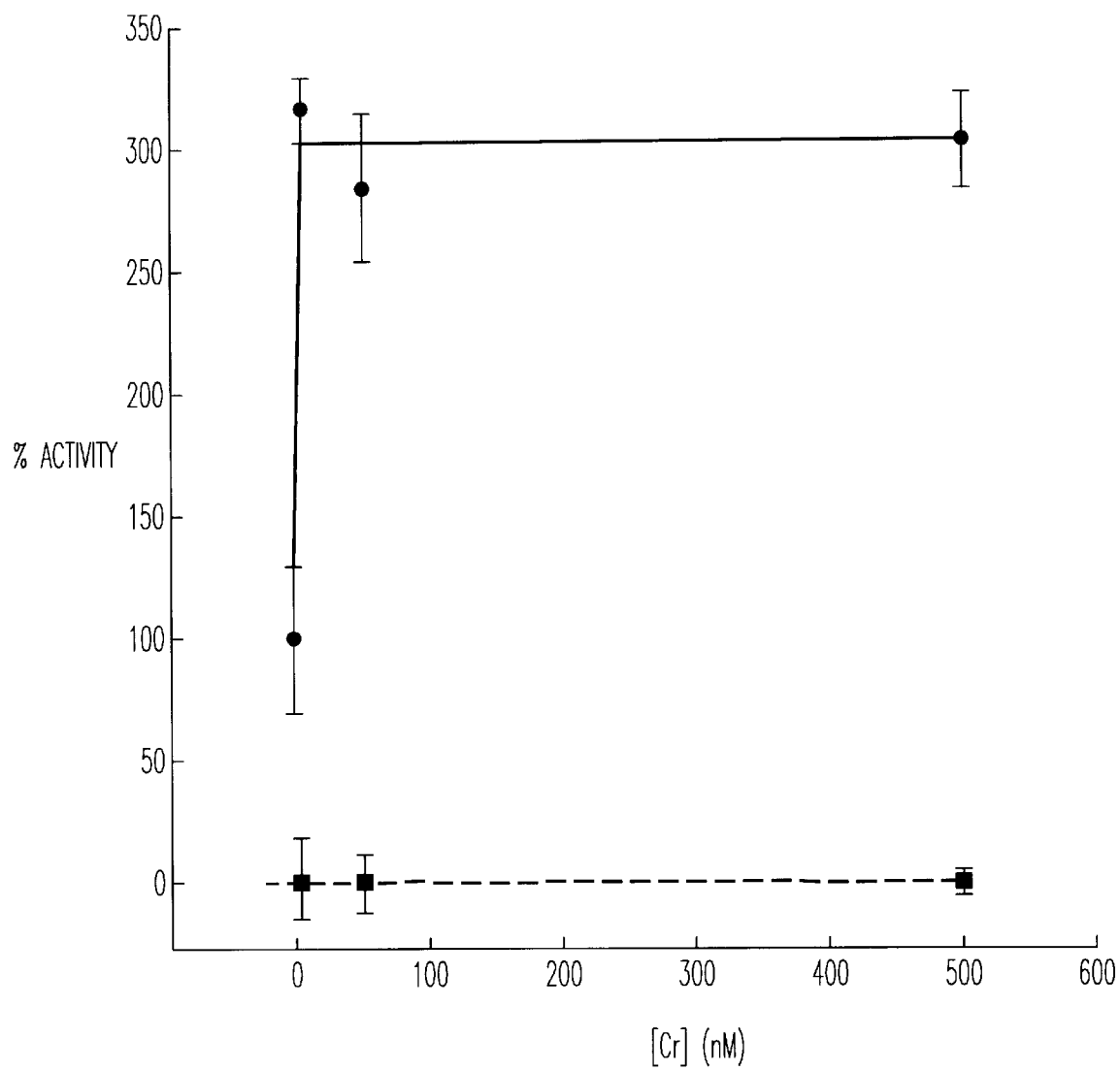

This hypothesis was tested by examining the activation of isolated rat insulin receptor by bovine liver LMWCr in the presence of insulin. As shown in FIG. 3, the addition of bovine liver LMWCr to isolated and purified rat liver insulin receptor amplifies the stimulation of receptor protein tyrosine kinase activity by insulin approximately seven fold. Fitting the activation curve to a hyperbolic function indicates that LMWCr interacts with the insulin-activated receptor with a dissociation constant of approximately 250 pM. Insulin receptor is the sit of LMWCr's action.

Figure 4:
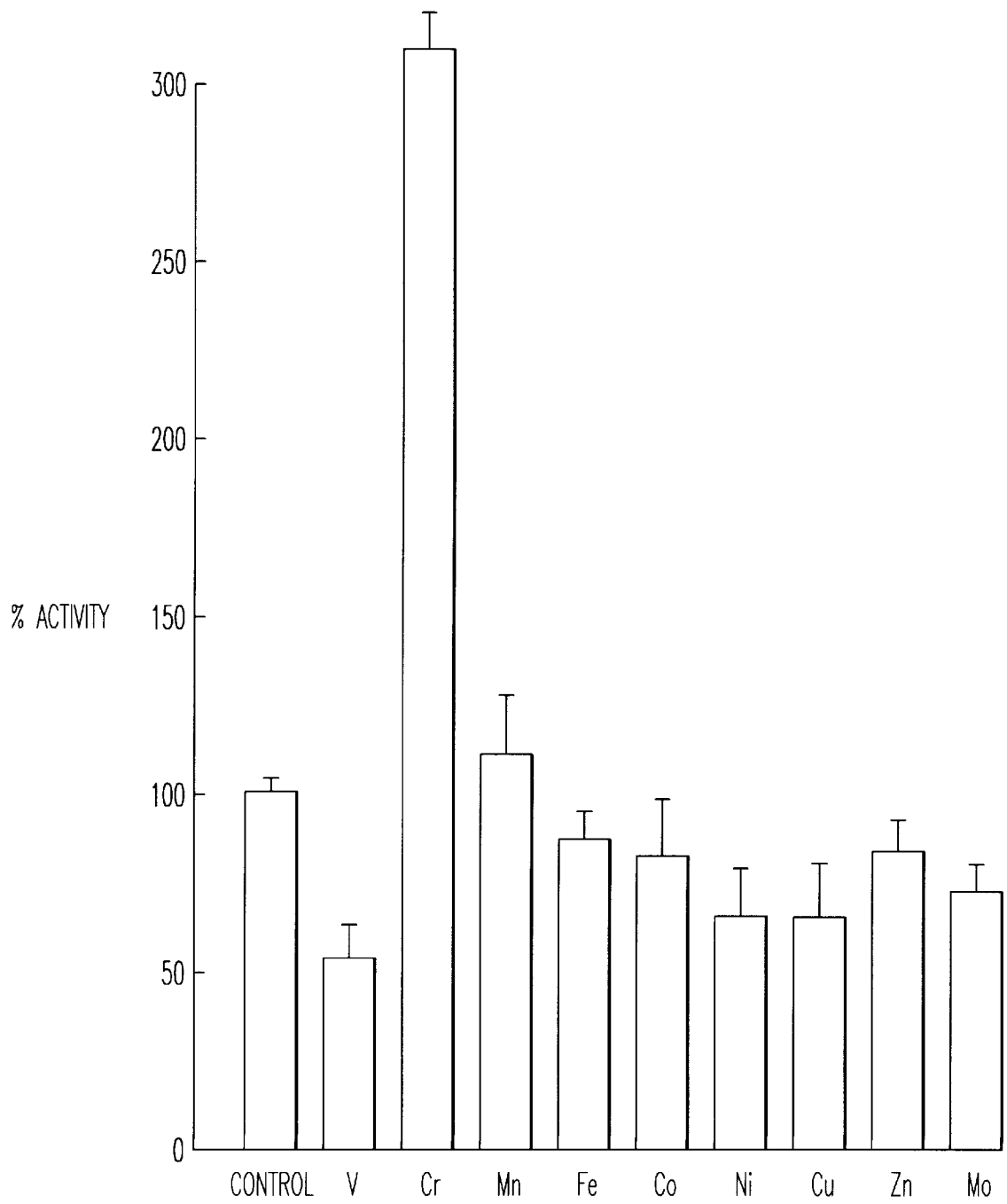
FIG. 4. Activation of rat adipocytic membrane protein tyrosine kinase activity using 0.75 μM gastrin fragment as substrate by apoLMWCr (125 nM) and metal ions (500 nM). 25 μL of a rat adipocytic membrane suspension corresponding to 40 μg protein/mL was utilized. Metal ions were incubated with the reaction mixture for 10 minutes at 37° C. prior to reaction initiation by addition of ATP.

Chromium plays a crucial role in the activation of insulin receptor kinase activity by LMWCr. ApoLMWCr (i.e., metal free) is inactive in the activation of insulin-dependent tyrosine kinase activity in the rat adipocyte membranes (FIG. 4). However, titration of apoLMWCr with chromic ions results in the total restoration of the ability to activate kinase activity; approximately four chromic ions per oligopeptide are required for maximal activity. This is consistent with the number of chromium (four per oligopeptide) reported to be bound to holoLMWCr from liver sources. Similarly, maximal activation of a rat adipocyte phosphotyrosine protein phosphatase by LMWCr requires four chromium per oligopeptide, while the ability of LMWCr to stimulate the insulin-dependent conversion of glucose to carbon dioxide by rat adipocytes has also been reported to be directly dependent on the chromium content of LMWCr (Yamamoto et al, 1989). This reconstitution of LMWCr's activation potential is specific to chromium. Transition metal ions commonly associated with biological systems are ineffective in potentiating the ability of apoLMWCr to activate kinase activity (FIG. 4). (In the absence of LMWCr, these transition metal ions also fail to demonstrate appreciable potential to activate the kinase activity in rat adipocyte membranes). Thus, the ability of LMWCr to potentiate the effects of insulin in stimulating the insulin-dependent protein tyrosine kinase activity of insulin receptor is specific to chromium and is directly dependent on the chromium content of LMWCr.

The results of this and other related studies are beginning to elucidate the biological function of LMWCr, which bears striking similarities to the role of calmodulin. (Calmodulin binds four calcium ions in response to a calcium flux; the tetracalcium form then binds to kinases and phosphatases stimulating their activity). Recent homeostasis studies have revealed that in response to increases in blood insulin concentrations chromium concentrations decrease as the metal is taken up by insulin-dependent cells. LMWCr is maintained in these cells almost entirely in its apo (metal free form). However, apoLMWCr has a large chromic ion binding constant; for example, LMWCr can remove Cr from Cr-transferrin. The ability of LMWCr to potentiate the effects of insulin or activate phosphotyrosine phosphatase or protein tyrosine kinase activity is directly dependent on its Cr(III) content and cannot be replaced by other transition metal ions. Thus, movement of chromium from the blood to insulin-sensitive tissues results in the formation of the holoLMWCr, possessing four chromic ions in a tetranuclear assembly. HoloLMWCr then binds with a dissociation constant on the order of 100 pM to 10 nM to at least protein tyrosine kinases and phosphotyrosine phosphatases, whose activities are subsequently stimulated.

Thus, insulin appears to stimulate an activation of LMWCr by initiating its loading with Cr, which in turn can potentiate insulin's effects. Therefore, it is not surprising that Cr deficiency has been found to be associated with non-insulin dependent diabetes and its symptoms and that, for example, Cr administration to streptotozotocin-induced diabetic rats resulted in enhanced insulin responsiveness while insulin receptor number remained constant. What is surprising is that for the first row transition elements from vanadium to zinc which are each essential for some form of life chromium is the only element for which previously at least metallobiomolecule containing the element had not been well characterized in terms of its function and mode of action.

Thus, the symptoms of adult-onset diabetes associated with chromium deficiency and attributed to apparent insulin resistance appear to stem from insufficient quantities of chromium to generate holoLMWCr in response to insulin or inability to properly synthesize or load LMWCr, such that insulin receptor kinase activity is not activated to an appropriate degree.

The identity of LMWCr can be tested in three manners. First, it has a simple organic composition being comprised of only glycine, glutamate, aspartate, and cysteine in known ratios. This can be readily tested for; unfortunately, the oligopeptide has not been sequenced due to numerous obstacles. Efforts are currently underway to work out the sequence. Secondly, the ability to stimulate insulin receptor phosphotyrosine protein kinase activity or rat adipocyte membrane phosphotyrosine protein kinase activity can be examined. Last, a more simple assay looking at the ability of LMWCr to stimulate the phophotyrosine protein phosphatase of rat adipocyte membranes or isolated Yersinia phosphotyrosine phosphatase active site fragment using para-nitrophenylphosphate as substrate.

Figure 5A:
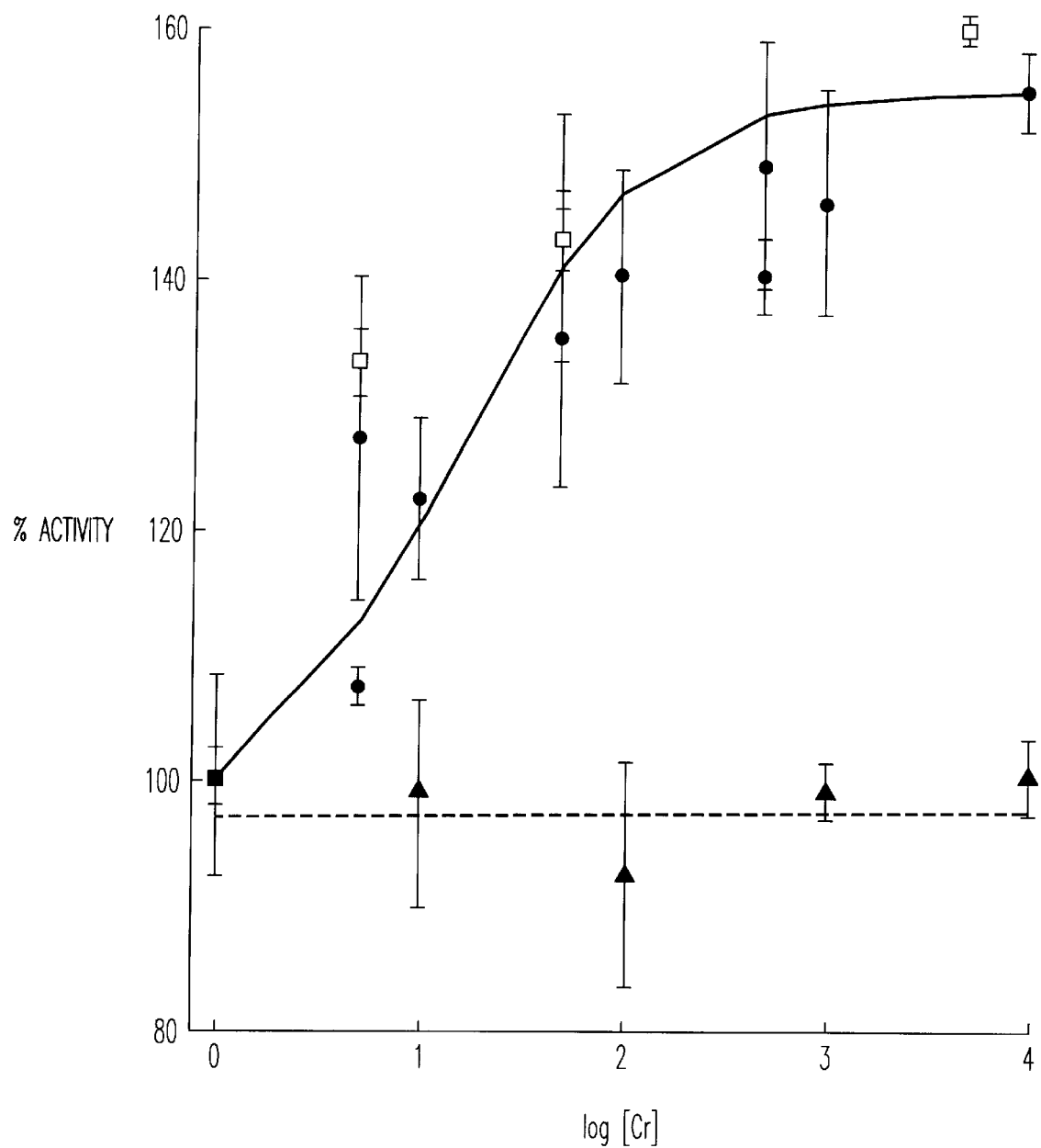
FIGS. 5A and 5B. 5A—Activation of rat adipocytic membrane phosphotyrosine phosphatase activity using 5 mM p-NPP as substrate by LMWCr (solid circles) and rat adipocytic membrane phosphoserine phosphatase activity using 0.83 mM phosvitin as substrate (shaded triangles). 125 μL of a rat membrane suspension corresponding to 136.8 μg protein/mL was utilized. Activation of phosphotyrosine phosphatase activity of Yersinia phosphotyrosine phosphatase fragment (19.5 milliunits) using 5 mM paranitrophenylphosphate (p-NPP) as substrate by LMWCr (open circles). The line is the best fit curve giving a LMWCr dissociation constant of 4.4 nM. 5(B) activation of rat adipocyte membrane phosphotyrosine phosphatase activity using 0.75 μM human gastrin fragment (open squares) or hirudin fragment (solid circles) as substrate. 125 μL of a rat membrane suspension corresponding to 129 μg protein/mL was utilized. The line is the same best fit curve as above. All Cr concentrations are presented in units of nM.
Figure 5B:
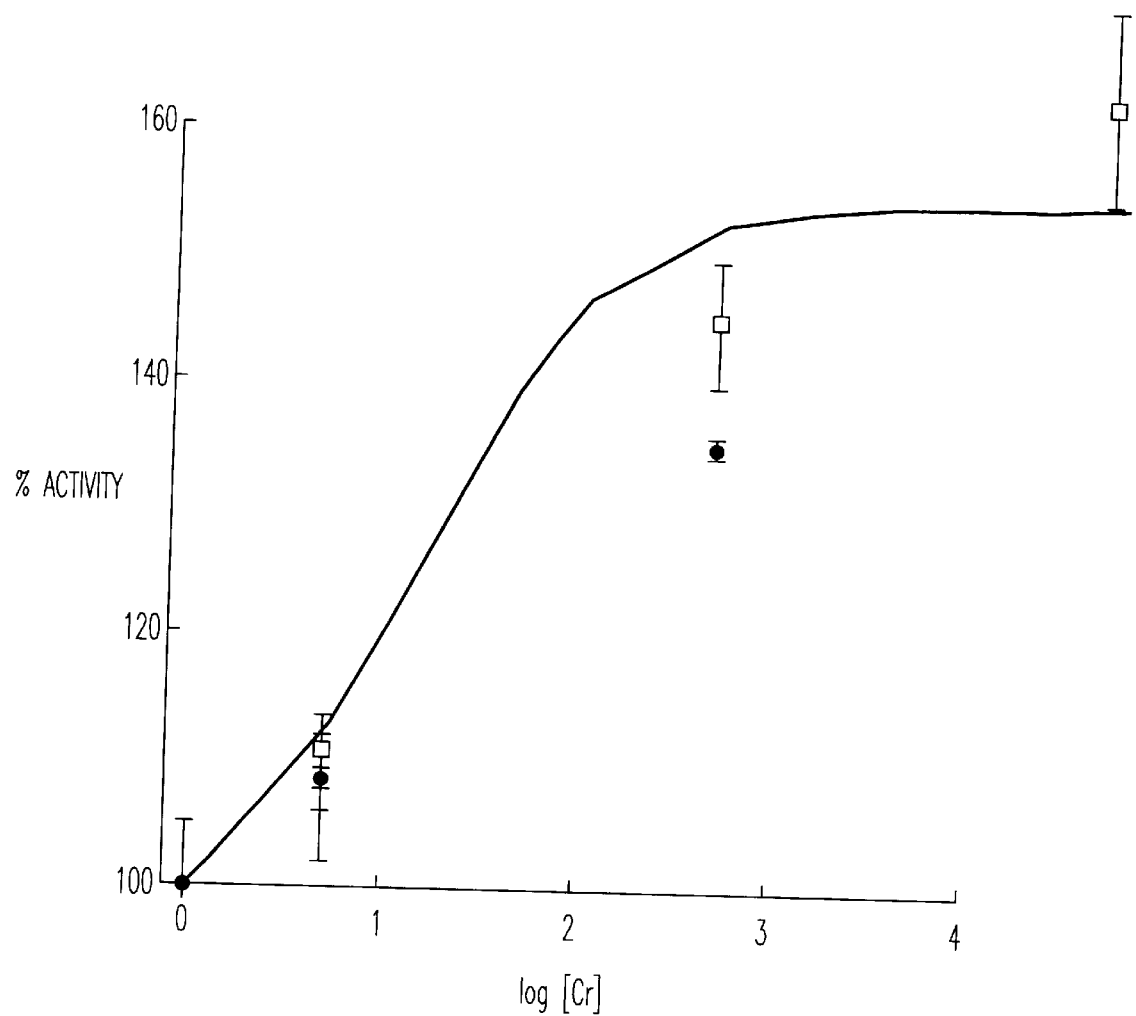

We have developed the last method and use it routinely to measure the viability of our LMWCr preparations, as it is much easier and especially much faster than performing the biological activity assays (with whole cells and carbon-14-labelled glucose). Rat adipocytes were homogenized and separated into three portions: lipids, soluble, and membrane/particulate. LMWCr had no effect on phosphatase activity towards p-NPP in either the lipid or soluble portions (not shown); however, a distinct effect was observed in the phosphatase activity associated with the membrane fragments (FIG. 5). The ammonium acetate buffer that LMWCr is stored in displayed no ability to activate the phosphatase activity, and LMWCr in the absence of the membranes also demonstrated no catalytic activity. Over the concentration range 0.1 nM to 10 $\mu$M (in terms of Cr), the addition of LMWCr activates the arylphosphate phosphatase activity of the membranes in a concentration dependent fashion. Fitting the hyperbolic phosphatase activation behavior to the Henri-Michaelis-Menton equation yields a LMWCr dissociation constant of 4.4 nM. Similar results over the same Cr concentration range have also been obtained utilizing adipocytes isolated from the adipose tissue trimmed from bovine liver.

To determine whether this arylphosphate phosphatase activity corresponded to phosphotyrosine phosphatase activity, the ability of LMWCr to activate the hydrolysis of phosphotyrosine-containing polypeptides was examined. Using human gastrin (amino acids 1–17) phosphorylated on tyrosine-12 and a synthetic fragment of hirudin (53–65 C terminal fragment) phosphorylated on tyrosine-63 as substrates and the adipocyte membrane fragments, LMWCr activated hydrolysis in a concentration dependent manner, nearly identical to that of p-NPP by the membrane fragments. These phosphotyrosine-containing peptide assays were performed in the presence of the kinase inhibitor piceatonnol, suggesting that phosphatase activation and not kinase inactivation is responsible for this activity. When the phosphoserine-containing protein phosvitin was used as a substrate, no activation of dephosphorylation of this protein was observed over the same range of LMWCr concentrations (FIG. 5). The activation potential of LMWCr is therefore likely to be directed towards phosphotyrosine phosphatase activity.

Rat adipocyte membranes posses a number of phosphatases including phosphoserine/phosphothreonine phosphatases (PP's) and phosphotyrosine phosphatases (PTP's). PP1 comprises 80% of phosphoserine/phosphothreonine phosphatase activity in rat adipocyte membranes, while PP2A is apparently restricted to the cytosol (Begum, 1995); rat adipocytes contains virtually no PP2B activity and only low levels of PP2C activity. To determine which type of phosphatase was activated by LMWCr, the effect of LMWCr on isolated phosphatases was examined. In the same concentration range used with the membrane fragments, LMWCr had no effect on alkaline phosphatase or phosphoprotein phosphatase 1 (PP1). In contrast, LMWCr activates the hydrolysis of $\rho$-NPP by the catalytic fragment of Yersinia phosphotyrosine phosphatase; the concentration dependence of the activation of the fragment is essentially identical to that of the membrane fragments (FIG. 5), indicating that LMWCr must be activating a PTP. The use of the isolated phosphatase clearly suggests that inactivation of a kinase is not responsible for the observed apparent dephosphorylation.

Apoprotein (which contains circa 0.3 Cr) activates PTP activity slightly (~33%), while addition of apoprotein and four equivalents of chromic ions completely restores the activation potential of the polypeptide. The activation by high concentrations of apoprotein suggests that only a tiny fraction of the protein still binding chromium is present in the form containing four Cr centers while the remainder probably contain inactive mononuclear chromium centers. Integration of EPR spectra of apoprotein (using hexaaquochromium(III) as standard) indicate that essentially all the chromium exists as mononuclear centers. Titration of apoprotein with chromium (III) reveals that 3.89 Cr/protein are required for complete restoration of the phosphatase activation activity. Chromic ions by themselves are ineffective. PTP activation is, thus, dependent on the Cr content. Hence, the metal would appear to be important in maintaining the proper conformation of the polypeptide. With the exception of ferric ions, transition metal ions commonly associated with biological systems (other than Cr) are ineffective in potentiating the ability of apoprotein to activate the PTP activity Even activation by ferric ions is extremely small although significant statistically ($P<0.0002$). LMWCr would appear then to be specific for $Cr^{3+}$. None of the metals examined in the absence of apoprotein resulted in activation of the phosphatase activity.

Incubation of rat adipocyte membranes with monoclonal antibodies whose epitope is the catalytic domain of human PTP1B and which react with rat PTP1B results in the reduction of LMWCr's ability to stimulate PTP activity; when using 50 $\mu$M Cr as LMWCr, the antibodies result in a loss of 78% of the oligopeptide's ability to potentiate PTP activity. Hence, the PTP(s) activated by LMWCr must be PTP1B and/or closely related phosphotyrosine protein phosphatases. This is also supported by studies using the isolated phosphotyrosine protein phosphatase LAR, which has distinct inhibition properties from PTP1A' and PTP1B; no activation of this enzyme's activity towards the dephosphorylation of $\rho$-NPP was observed over a range of LMWCr concentration (Cr concentrations varying from 5 nM to 5 $\mu$M).

Therefore, preparations which may contain LMWCr can be separated by size using size exclusion chromatography or HPLC. Species of similar molecular weight to LMWCr can be analyzed for chromium content. Chromium containing species could be further purified or tested for activity using the phosphatase assay (or even insulin dependent kinase activity assay) . The nature of the material could also be tested against LMWCr amino acid content.

LMWCr is the actual species in mammals responsible for the biological activity of chromium; it is not an artificial species from which the body must remove the Cr and then put the Cr in the correct place. Medical conditions which could arise from an inability to produce or process LMWCr would not be aided by the above Cr sources. LMWCr does not contain picolinate and should, thus, not lead to picolinate-derived chromosome damage. It does not possess an unpleasant odor and can be isolated from cheap materials, i.e. bovine liver.

Chromium complexes are currently recommended in daily dosages of 100–200 micrograms of chromium per person. A recommended safe and adequate daily intake of chromium is at least 50 micrograms. At levels of 100 micrograms of chromium per person, per day, chromium can be used as a supplement to a chromium-deficient diet, to replace the large chromium losses associated with exercise, weight-training and muscle building, and to replace chromium losses associated with aging and in the treatment and prevention of glucose intolerance, of atherosclerotic and other cardiovascular diseases, of hypercholesteremic conditions by lowering low-density lipoprotein cholesterol while increasing high-density lipoprotein cholesterol, and in the treatment and prevention of adult-onset diabetes. While individual needs will vary, LMWCr is effective at amounts between 25–2000 micrograms chromium per day, in light of its greater activity than available Cr sources.

PROTEIN PURIFICATION:

LMWCr was isolated from bovine liver. Although procedures for isolation from other mammals are known, e.g., *Tamamoto et al, Eur. J. Biochem.*, 165, 627–631 (1987), several important modifications were required. LMWCr was extracted from 1 kg of diced bovine liver suspended in 1 L water containing 3.4 mmol $K_2Cr_2O_7$ (and protease inhibitors when necessary) and homogenized in a Waring blender for one minute at high speed. The homogenate was centrifuged at 11,000 g for 10 min. at 4° C. to remove cell debris. All subsequent operations were performed at 4° C. unless otherwise stated. An equal volume of ethanol was added to the supernatent; the resulting slurry was stirred overnight, before being centrifuged at 11,000 g for 10 minutes. The supernatant was made 90 percent in ethanol and allowed to stir for 2 days. The resulting light brown precipitate was collected by centrifugation at 4,200 g for 5 minutes. The precipitate was then freeze-dried to give a golden brown to green-brown solid. The resulting solid was extracted with a minimum of water and briefly centrifuged to remove any undissolved debris; the extract was also then filtered through glass wool to remove any additional particles and avoid plugging the chromatography column in the subsequent step. The clear greenish-brown filtrate was loaded onto a 2.5× circa 80 cm column of DEAE cellulose (Whatman) equilibrated with 0.2M $NH_4OAc$ buffer, pH 7.2. The protein concentration on this and subsequent columns was monitored using the absorbance at 260 nm. Fractions containing the major Cr-containing band were pooled and concentrated by ultrafiltration (Amicon 8010 using YCO5 membrane). The concentrated solution was diluted with an equal volume of water and applied again to an identical DEAE column, equilibrated with 0.2M $NH_4OAc$ buffer, pH 7.2. The column was washed and eluted as previously described. Chromium-rich fractions (representing a distinct gray-green band) were again pooled and concentrated to circa 20 mL by ultrafiltration. The gray-green solution is applied to a Sephadex G-25 column (2.5×80 cm) and eluated with 0.050M $NH_4OAc$, pH 6.5. Gray-green, chromium-containing fractions are collected and concentrated by ultrafiltration (Amicon 8010 and/or 8400 with YCO5 membrane) to less than 10 mL. The deep gray-green solution is applied to Sephadex G-15 (6.5×60 cm) column and eluted with 0.050 $NH_4OAc$, pH 6.5. Gray-green fractions are again collected and concentrated and reapplied to the G-15 column as described above. The resulting LMWCr solution is concentrated by ultrafiltration and lyophilization and stored at −20° C. For HPLC, Shodex OH PAK B-803 and B-800P columns (Shoko. Co., Ltd.) were utilized; mobile phase was 0.1M NaCl.

This invention has been disclosed by specific example, as well as generic description. Variations will occur to those of skill in the art, including variations as to homogenization conditions, separation conditions, specific in vitro addition, etc., as well as specific dosage ranges, without the exercise of inventive faculty. These variations remain within the scope of the invention disclosed herein, save for their exclusion by express recitations of the claims set forth below.

What is claimed is:

1. Isolated, purified bovine liver low-molecular weight chromium-binding protein (LMWCr).

2. The bovine liver LMWCr of claim 1, wherein said LMWCr bears its full complement of chromium.

3. A method of isolating purified bovine liver LMWCr, comprising homogenizing bovine liver with one volume of water containing a chromium source selected from the group consisting of a chromium (VI) source, a chromium (III) source and mixtures thereof, fractionating said homogenate with sequential ethanol precipitations, to obtain fractions containing LMWCr, subjecting said fractions to ion-exchange chromatography, followed by size-exclusion chromatography, and purifying the LMWCr obtained therefrom through HPLC chromatography.

4. The method of claim 3, wherein said chromium source added in said homogenization step comprises 3.4 mmoles of chromium, as dichromate, per two liters of homogenate.

5. A method of supplementing a chromium-deficient diet of a human individual comprising:

administering to said individual Cr in the form of the LMWCr of claim 2 in amounts of 25–2000 micrograms Cr per day.

6. A method of treating at least one of glucose intolerance, atherosclerotic cardiovascular disease, hypercholesteremic condition, and adult-onset diabetes in a human patient, comprising administering to said patient 25–2000 micrograms Cr, per day, in the form of the LMWCr of claim 2.

7. A dietary supplement sufficient to replace chromium losses associated with exercise, weight training, and muscle building, comprising, as an active agent, 25–2000 micrograms Cr, per day, in the form of the LMWCr of claim 2, in a pharmaceutically acceptable carrier.

* * * * *

UNITED STATES PATENT AND TRADEMARK OFFICE
CERTIFICATE OF CORRECTION

PATENT NO. : 5,872,102
DATED : February 16, 1999
INVENTOR(S) : John B. Vincent, et al.

It is certified that error appears in the above-identified patent and that said Letters Patent is hereby corrected as shown below:

Column 3, Line 20 and 21, "(N-2hydroxyethylpiperazine-N'-2-ethanesulfonic acid)" should read --(N-2-hydroxyethylpiperazine-N'-2-ethanesulfonic acid)--.

Column 4, Line 18, "3.4 mm" should read --3.4 mmol--.

Column 5, Line 41, "a" should read --$\alpha$--.

Column 10, Line 1, "eluated" should read --eluted--.

Signed and Sealed this

Twenty-seventh Day of July, 1999

Attest:

Q. TODD DICKINSON

*Attesting Officer*  *Acting Commissioner of Patents and Trademarks*